US008138289B2

(12) United States Patent
Kofinas et al.

(10) Patent No.: US 8,138,289 B2
(45) Date of Patent: Mar. 20, 2012

(54) IMPRINTED POLYMERIC MATERIALS FOR BINDING VARIOUS TARGETS SUCH AS VIRUSES

(75) Inventors: Peter Kofinas, North Bethesda, MD (US); Daniel Janiak, Bethesda, MD (US)

(73) Assignee: University of Maryland, College Park, College Park, MD (US)

( * ) Notice: Subject to any disclaimer, the term of this patent is extended or adjusted under 35 U.S.C. 154(b) by 763 days.

(21) Appl. No.: 12/048,995

(22) Filed: Mar. 14, 2008

(65) Prior Publication Data

US 2008/0241185 A1 Oct. 2, 2008

Related U.S. Application Data

(60) Provisional application No. 60/908,279, filed on Mar. 27, 2007.

(51) Int. Cl.
*C08F 20/00* (2006.01)
(52) U.S. Cl. .................... 526/303.1; 264/220; 264/221; 264/222
(58) Field of Classification Search ............... 526/303.1; 264/220, 221, 222
See application file for complete search history.

(56) References Cited

U.S. PATENT DOCUMENTS

| 6,379,599 B1 * | 4/2002 | Vaidya et al. ................. 264/220 |
| 6,670,427 B1 | 12/2003 | Ulbricht et al. |
| 2004/0126814 A1 | 7/2004 | Singh et al. |
| 2004/0192869 A1 | 9/2004 | Kulkarni et al. |
| 2008/0038832 A1 | 2/2008 | Sellergren et al. |

FOREIGN PATENT DOCUMENTS

| DE | 10 2004 049 805 A1 | 4/2006 |
| WO | WO 01/25291 | 4/2001 |
| WO | WO 2006/129088 A1 | 12/2006 |

OTHER PUBLICATIONS

Bolisay, L.D., et al., "Molecularly imprinted polymers for tobacco mosaic virus recognition," *Biomaterials* 27:4165-4168, Elsevier Ltd., Netherlands (2006).
Parmpi, P. and Kofinas, P., "Biomimetic glucose recognition using molecularly imprinted polymer hydrogels," *Biomaterials* 25:1969-1973, Elsevier Ltd., Netherlands (2004).
Wizeman, W. and Kofinas, P., "Molecularly imprinted polymer hydrogels displaying isomerically resolved glucose binding," *Biomaterials* 22:1485-1491, Elsevier Science Ltd., Netherlands (2001).
International Search Report for International Application No. PCT/US2008/057048, European Patent Office, Netherlands, mailed Sep. 30, 2008.

* cited by examiner

*Primary Examiner* — Edward Cain
(74) *Attorney, Agent, or Firm* — Sterne, Kessler, Goldstein & Fox P.L.L.C.

(57) ABSTRACT

Imprinted polymeric materials that selectively bind to a template article. Various types of template articles may be targeted by the imprinted polymeric materials, including microorganisms (e.g., viruses or bacteria) or biologic macromolecules (e.g., proteins or DNA). The imprinted polymeric material may be formed by template-directed synthesis using monomer units that interact with the template article. The monomer units are used to form a polymer matrix around the template article. Subsequently, the template article is removed from the polymer matrix. Also disclosed are imprinted polymeric materials comprising a cross-linked polymer matrix, which comprises a polyampholyte polymer. The polymer matrix has a binding cavity capable of selectively binding to a template article. Also disclosed are various uses for such imprinted polymeric materials.

45 Claims, 5 Drawing Sheets

IMPRINTED POLYMERIC MATERIALS FOR BINDING VARIOUS TARGETS SUCH AS VIRUSES

CROSS-REFERENCES TO RELATED APPLICATIONS

This application claims the benefit of U.S. provisional application Ser. No. 60/908,279 (filed 27 Mar. 2007), which is incorporated by reference herein.

GOVERNMENT RIGHTS

Using the specific language required by 37 C.F.R. §401.14 (f)(4): This invention was made with government support under grant numbers CTS-03-03951 and CTS-06-40778 awarded by the National Science Foundation and grant number 2005-35603-16278 awarded by the U.S. Department of Agriculture. The government has certain rights in the invention.

TECHNICAL FIELD

The present invention relates to molecularly imprinted polymeric materials.

BACKGROUND

The ability to separate and/or purify viruses has enormous potential benefits in medicine, public health, and biotechnology. For example, the process of manufacturing vaccines involves the separation and purification of viruses from raw preparations (e.g., viruses harvested from infected chicken eggs or cell cultures). In fact, this separation and purification process can account for a large percentage of the production cost in the manufacture of a vaccine. In many cases, the purification of a virus involves multiple steps (which can take days), including the steps of: extraction, precipitation, centrifugation, suspension, ultracentrifugation, and resuspension performed sequentially to obtain a virus preparation suitable for use in vaccine production. Thus, a more efficient technique for the separation and purification of viruses could lower the cost and reduce the time associated with vaccine manufacture.

In another example, in patients infected with the HIV virus, reducing viral loads is an important aspect to treatment. Conventionally, antiviral medications are administered to the HIV-infected patient to reduce viral loads. However, many such antiviral medications have serious adverse side effects. As such, the ability to separate and extract viruses from a patient's bloodstream could provide an alternative modality of treatment for HIV infection.

SUMMARY

In one aspect, the present invention provides an imprinted polymeric material comprising a cross-linked polymer matrix having a binding cavity capable of selectively binding a template article, wherein the polymer matrix comprises a polyampholyte polymer.

In another aspect, the present invention provides a method of forming an imprinted polymeric material, comprising: (a) providing a template article in an aqueous solution; (b) adding a first monomer unit to the aqueous solution, wherein the first monomer unit exhibits an electrostatic charge in the aqueous solution; (c) adding a second monomer unit to the aqueous solution, wherein the second monomer unit is different from the first monomer unit; (d) forming a polymer matrix containing the template article, wherein the step of forming the polymer matrix comprises polymerizing the monomer units; and (e) removing the template article from the polymer matrix. In some cases, the method further comprises adding a third monomer unit to the aqueous solution, wherein the third monomer unit is different from both the first monomer unit and the second monomer unit.

In other aspects, the present invention provides various uses for the imprinted polymeric material.

DETAILED DESCRIPTION

The present invention provides imprinted polymeric materials that are designed to selectively bind with a template article. Various types of template articles may be targeted by the imprinted polymeric materials, including microorganisms (e.g., viruses or bacteria) or biologic macromolecules (e.g., proteins or DNA).

In one aspect, the present invention provides a method of forming such an imprinted polymeric material by template-directed synthesis. The method involves mixing the template article in an aqueous solution (e.g., a buffer solution) with monomer units that interact with functional groups on the template article. The monomer units may interact with the template article through any of various types of bonding mechanisms, including ionic, hydrophilic/hydrophobic, steric, electrostatic, hydrogen bonding, van der Waals forces, metal coordination, or other types of interactions. In some cases, the monomer units may have functional groups that participate in this interaction, including such functional groups as amines, hydroxyls, carboxyls, sulfhydryls, metal chelates, and multiple combinations of any of the these (e.g., dicarboxylates, diamines, etc).

In certain embodiments, the monomer units are capable of exhibiting an electrostatic charge in an aqueous solution. In some cases, the monomer units may be acidic or basic, which under the appropriate pH conditions, exhibit a negative or positive electrostatic charge, respectively. The acid/base monomer units may have varying levels of acidity/basicity, which will determine the extent to which the monomer units will be present in the anionic/cationic form at the pH level of the aqueous solution. With respect to acidic monomer units, the monomer unit may be a strong acid (in which its ability to exhibit a negative charge is largely pH independent) or a weak acid (in which its ability to exhibit a negative charge is pH dependent). With respect to basic monomer units, the monomer unit may be a strong base (in which its ability to exhibit a positive charge is largely pH independent) or a weak base (in which its ability to exhibit a positive charge is pH dependent).

Examples of monomer units that are strong acids include those having phosphonic or sulfonic acid groups, such as 2-acrylamidopropyl-2-methylpropane sulfonic acid (AMPSA). Examples of monomer units that are weak acids include those having carboxyl groups, such as acrylic acid, maleic acid, 2-aminomethacrylate hydrochloride (AMA), and 2-dimethylaminoethyl methacrylate (DMAEMA). Examples of monomer units that are strong bases include those having ammonium groups, such as 3-acrylamidopropyl trimethylammonium chloride (AMPTAC). Examples of monomer units that are weak bases include those having amino groups, such as 3-N-aminopropylmethacrylamide and dimethyl aminoethylmethacrylate. The monomer units may also be neutral monomers exhibiting no electrostatic charge in the solution. Examples of such monomers include acrylamide (Am), N-tertbutylacrylamide (NTBAAm), N-isopropylacrylamide (NIPAAm), and N,N'-dimethylacrylamide (DMAAm).

The monomer units may also have other characteristics which will determine its ability to interact with the template article, such as its hydrophilicity/hydrophobicity or spatial structure. Thus, the monomer units can be selected on the basis of these various characteristics for a favorable interaction with the template article. For example, a hydrophilic monomer unit exhibiting a positive charge in the aqueous solution can be selected for its ability to interact favorably with a portion of the template article that is hydrophilic (through hydrophilic interactions) and negatively-charged (through electrostatic attraction).

The pH level of the aqueous solution containing the template article and monomer units can vary according to the particular application. Because the charges on the template article and the charge-carrying ability of the monomer units can vary according to the pH level of the aqueous solution (especially for monomer units with functional groups that are weak acids or bases), the pH level can be adjusted to achieve the desired electrostatic charge characteristics on the template article and/or monomer units.

In certain embodiments, one or more different types of monomer units may be used in combination. For example, an acidic monomer unit, a basic monomer unit, and a neutral monomer unit may be used in combination. This feature may be useful in synthesizing an imprinted polymeric material for binding biological materials (e.g., microorganisms such as viruses, or macromolecules such as proteins) which often exhibit a mixture of different charges in solution. In this case, the acidic monomer units (present in anionic form in the solution) may interact with portions of the template article that exhibit a positive electrostatic charge; the basic monomer units (present in cationic form in the solution) may interact with portions of the template article that exhibit a negative electrostatic charge; and the neutral monomer units may interact with portions of the template article having no charge.

Furthermore, in some cases, the molar ratios of each different type of monomer unit may be substantially complementary to the ratio of the charges on the template article in the solution. For many viruses, the amino acid structure of the viral capsid or envelope proteins are known. As such, the ratio of neutral, negative, and positive charges on the viral capsid or envelope protein can be determined (for a given pH), and the different monomer units can be provided at molar ratios that substantially complement this charge ratio on the viral capsid protein. Also, the amino acid structure of many other types of proteins are known, and as such, the ratio of neutral, negative, and positive charges on the protein can be determined (for a given pH), and the different monomer units can be provided at molar ratios that substantially complement this charge ratio on the protein.

Where different types of monomer units are used in combination, the different monomer units may be mixed together with the template article simultaneously or in sequence. Sequential addition of the different monomer units may be useful in avoiding interactions between the different monomer units (e.g., between monomer units having opposite charges), which can interfere with the interaction between the monomer units and the template article.

By their interaction with different parts of the template article, the monomer units are distributed around the template article. Once organized in this fashion, the monomer units are fixed into place by polymerization (which includes co-polymerization if different monomer units are involved), and in some cases, by further cross-linking of the resulting polymers. Polymerization of the monomer units can be achieved using any of various techniques known in the art, including chemical processes (e.g., using free-radical initiators and/or catalysts), photochemical processes (e.g., exposure to UV-irradiation), or electrochemical processes. Likewise, cross-linking can be achieved using any of various techniques known in the art, including the addition of a cross-linking agent to the solution. In some cases, polymerization may be effected by the addition of ammonium persulfate (APS) as the polymerization initiator and N,N,N',N'-tetramethylethylenediamine (TEMED) as the cataylst. In some cases, the cross-linking agent is a difunctional monomer, N,N'-methylenebisacrylamide (BIS), epichlorohydrin (EPI), or ethylene glycol diglycidyl ether (EDGE). Polymerization and cross-linking may take place simultaneously or sequentially in any order. As such, the polymerization initiator, catalyst, and/or cross-linking agent may be added to the solution simultaneously or sequentially in any order.

In cases where a combination of monomer units having different charge properties are used, the resulting polymer may be a polyampholyte polymer. As used herein, a "polyampholyte polymer" refers to charged polymers with both acidic and basic functional groups (as well as neutral monomer units), such that under the appropriate pH conditions, the polymer will have both positive and negative charges. As such, as explained above, polyampholyte polymers may be useful in interacting with template articles that exhibit a mixture of different charges in solution (e.g., biological materials, including microorganisms such as viruses, or macromolecules such as proteins). Also, as explained above, the ratio of each type of charge (positive, negative, or neutral) on the polyampholyte polymer may be substantially complementary to the ratio of the charges on the template article in the solution.

Upon polymerization (and cross-linking, in some cases) of the monomer units, a polymer matrix is formed around the template article. As a result, the polymer matrix around the template article has functional groups that are positioned at locations where they are aligned with complementary functional groups on the template article. The template article is then removed from the polymer matrix using any of various extraction techniques, including solvent washing (e.g., with an acid, base, surfactant, buffer, or ionic solution) or chemical cleavage.

Figure 1A:
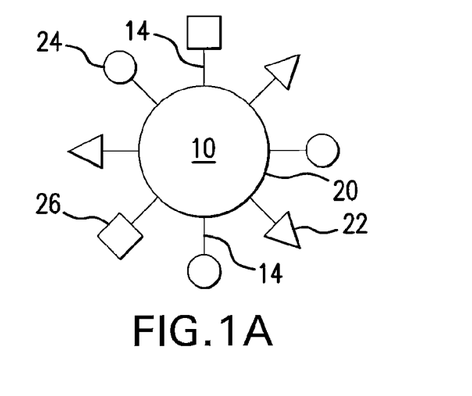
FIGS. 1A-1F show a schematic representation of a method of template-directed synthesis to create an imprinted polymeric material according to an embodiment of the present invention.

For example, FIGS. 1A-1F show one embodiment of the present invention for forming an imprinted polymeric material by template-directed synthesis. Referring to FIG. 1A, a virus 10 has a virus capsid 20 lined with capsid proteins 14. Each capsid protein 14 can have many different functional groups, but for simplification, only a single functional group (22, 24, or 26) is shown for each of capsid proteins 14. Each functional group 22, 24, and 26 has a different electrochemical property (represented here conceptually by their different shapes). Virus 10 is provided in an aqueous solution having a pH level such that functional group 22 has a negative charge, functional group 24 has a positive charge, and functional group 26 has no charge (neutral).

Three different types of monomer units are provided to interact with virus 10: a basic monomer unit 30 exhibiting a positive charge in the pH of the aqueous solution; an acidic monomer unit 34 exhibiting a negative charge in the pH of the aqueous solution; and a neutral monomer unit 32 having no charge. If the amino acid structure of virus capsid protein 14 is known, then the ratio of neutral, negative, and positive charges on viral capsid protein 14 can be determined (at the pH of the aqueous solution). As such, the molar ratio of the different monomer units can be selected to complement this charge ratio on viral capsid protein 14. For example, if virus capsid protein 14 is determined to have a charge ratio of 5(neutral):3(positive):2 (negative), then the molar ratios of the monomer units may be 5 (neutral):3 (negative):2(positive).

Figure 1B:
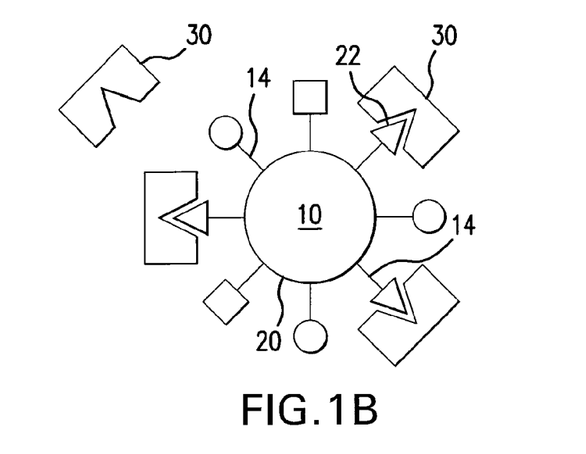
Figure 1C:
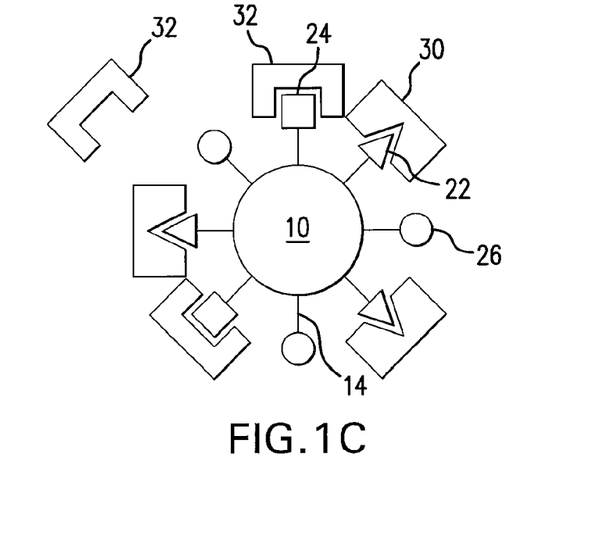
Figure 1D:
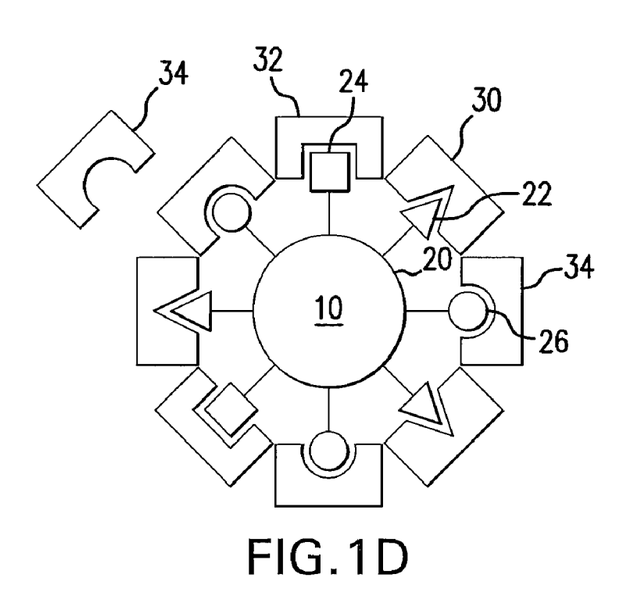

Referring to FIG. 1B, positively-charged (basic) monomer units 30 are added to the solution containing virus 10. Positively-charged monomer units 30 then associate with negatively-charged functional groups 22 on viral capsid proteins 14. Next, referring to FIG. 1C, neutral monomer units 32 are added to the solution mixture. Neutral monomer units 32 then associate with neutral functional groups 24 on viral capsid proteins 14. Next, referring to FIG. 1D, negatively-charged (acidic) monomer units 34 are added to the solution mixture. Negatively charged monomer units 34 then associate with positively-charged functional groups 26 on viral capsid proteins 14. As a result, monomer units 30, 32, and 34 are organized around virus 10 in a manner that complements the distribution of charges on the capsid 20 of virus 10.

Figure 1E:
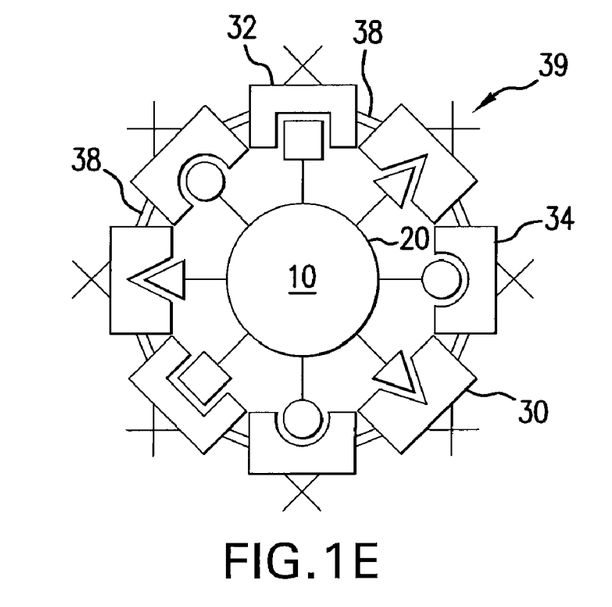
Figure 1F:
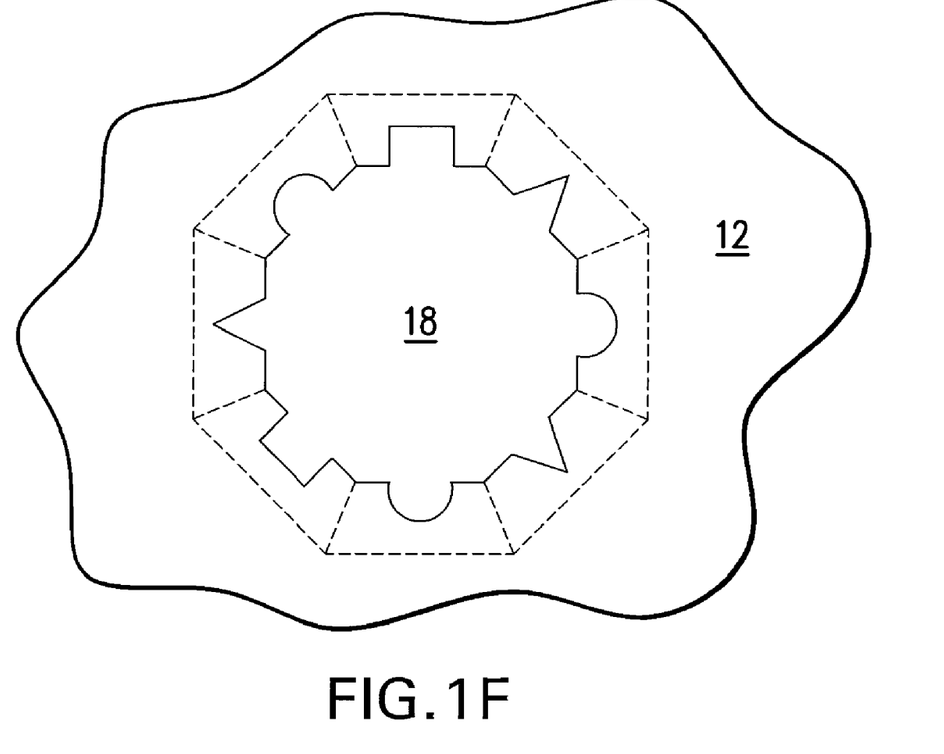

Next, referring to FIG. 1E, a polymerization initiator and cross-linking agent 39 are added to the solution mixture. The polymerization initiator causes the polymerization of the monomer units (via covalent links 38) to form polyampholyte polymer chains. Cross-linking agents 39 serves to cross-link the polymer chains (internally within a polymer chain, externally with other polymer chains, or both).

After polymerization and cross-linking, virus 10 is removed by solvent washing. As a result, referring to FIG. 1F, an imprinted polymeric material having a cross-linked polymer matrix 12 is formed. Polymer matrix 12 has a cavity 18 (now vacated by virus 10). Cavity 18 has a geometry (including its size and shape) that is complementary to that of virus 10. Also, the polymer matrix has functional groups that are positioned at locations around cavity 18 where they are aligned with complementary functional groups on virus 10. Thus, the resulting imprinted polymeric material is capable of selectively and reversibly binding virus 10.

In another aspect, an embodiment of the present invention provides an imprinted polymeric material comprising a cross-linked polymer matrix having a binding cavity capable of selectively binding a template article, wherein the cross-linked polymer matrix comprises a polyampholyte polymer. This imprinted polymeric material may be synthesized using any of various techniques, including those described above.

The binding cavity may have a geometry (including its size and shape) that is complementary to the template article. The shape of the binding cavity will vary depending on the template article. For example, viruses are known to have various shapes, including spherical, icosahedral, or rod-like. As such, where the template article is a virus, the shape of the binding cavity can be spherical, icosahedral, or rod-like. The size of the binding cavity will also vary depending upon the template article. In some cases, the size of the binding cavity (as measured along its longest axis) can range from 1 nm-1 μm. In some cases, the size of the binding cavity (as measured along its longest axis) can range from 10 nm-500 nm; binding cavities having a size in this range may be useful for selectively binding viruses, which generally also have a size in this range. The binding cavity may be contained in the polymer matrix at any of various locations, including within the polymer matrix (e.g., completely enclosed within the polymer matrix) or at a surface of the polymer matrix (e.g., partially enclosed by the polymer matrix).

Figure 2:
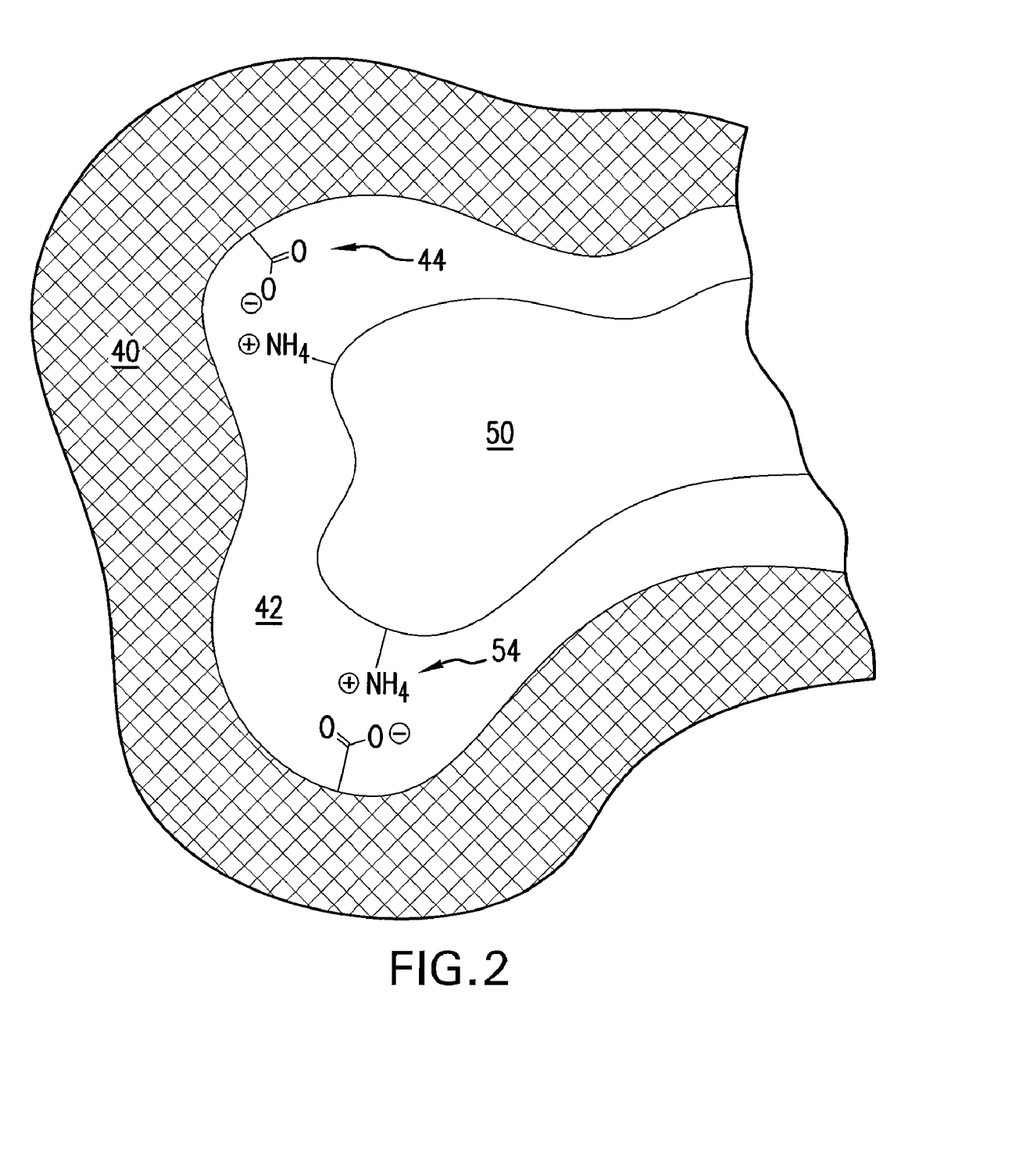
FIG. 2 shows a polymer matrix having a binding cavity containing a viral capsid protein, according to another embodiment.

The polymer matrix around the binding cavity has functional groups that are positioned at locations where they can align with complementary functional groups on the template article. The functional groups on the polymer matrix may interact, coordinate, or otherwise bond with the template article through various mechanisms, including ionic, hydrophilic/hydrophobic, steric, electrostatic, hydrogen bonding, or other types of interactions. For example, FIG. 2 shows a polymer matrix 40 having a binding cavity 42. A viral capsid protein 50 (on a virus) extends into binding cavity 42. Binding cavity 42 has a geometry that complements the geometry of viral capsid protein 50. Furthermore, negatively-charged carboxyl groups 44 on polymer matrix 40 are located around binding cavity 42 at positions where they are aligned with positively-charged amine groups 54 on viral capsid protein 50.

As explained above, the polyampholyte polymer may have any of various combinations of strong acids, weak acids, strong bases, weak bases, or neutral moieties as its constituent monomers. As such, the composition of the polyampholyte polymer can be selected to optimize its interaction with the template article. For example, where the template article is a virus, the polyampholyte polymer can be designed to exhibit a mixture of charges (positive, negative, and neutral) at a ratio that is substantially complementary to the ratio of the charges on the template article in the solution (at a given pH). Because the cross-linked polymer matrix comprises a polyampholyte polymer, in some cases, the polymeric material may be a hydrogel. In such cases, the binding cavity may be sufficiently rigid to retain its selective binding capability despite water-swelling of the polymer matrix. This property may be achieved by selecting the appropriate composition of the polyampholyte polymer or the reaction conditions used in making the polymeric material (e.g., amount and type of cross-linking).

The imprinted polymeric material can have various binding capacities for the template article. For example, the binding capacity of the imprinted polymeric material for the template article may be at least 2-fold greater; and in some cases, at least 4-fold greater; and in some cases, at least 6-fold greater, than the binding capacity of a control polymeric material with a cross-linked polyampholyte polymer matrix which lacks a binding cavity capable of binding selectively to the template article (i.e., a "blank" polymeric material which is synthesized in the absence of a template article).

"Selectively binding" refers to the preferential binding exhibited by the imprinted polymeric material for the template article as compared to a non-template article having a different geometric structure. Where the template article is a virus, the imprinted polymeric material will preferentially bind the target virus as compared to another virus having a different geometric (including its size and shape) structure. For example, where the template article is the tobacco mosaic virus (TMV), the imprinted polymeric material will preferentially bind TMV as compared to the tobacco necrosis virus (TNV), which has a different geometric structure. In another example, where the template article is a protein, the imprinted polymeric material will preferentially bind the target protein as compared to another type of protein having a different amino acid sequence and tertiary structure. Selective binding includes both affinity and specificity of the imprinted polymeric material for the template article.

The imprinted polymeric material may possess various degrees of binding selectivity for the template article. One way of measuring binding selectively is the difference in the binding capacity of the imprinted polymeric material for the template article as compared to its binding capacity for a non-template article having a different geometric structure. As such, where the template article is a virus, binding selectivity can be measured by the difference in the binding capacity of the imprinted polymeric material for the target virus as compared to another virus having a different geometric structure. For example, the imprinted polymeric material may have a binding capacity for the target virus that is at least 2-fold greater; and in some cases, at least 4-fold greater; and in some cases, at least 6-fold greater, than its binding capacity for another virus having a different geometric structure.

The imprinted polymeric materials of the present invention may have various uses. Such uses include separation/purification of the template article or sensing/detection (e.g., in medical diagnostics) of the template article in a sample. As such, in other aspects, the present invention provides various possible uses for the imprinted polymeric materials.

Figures 3A, 3B:
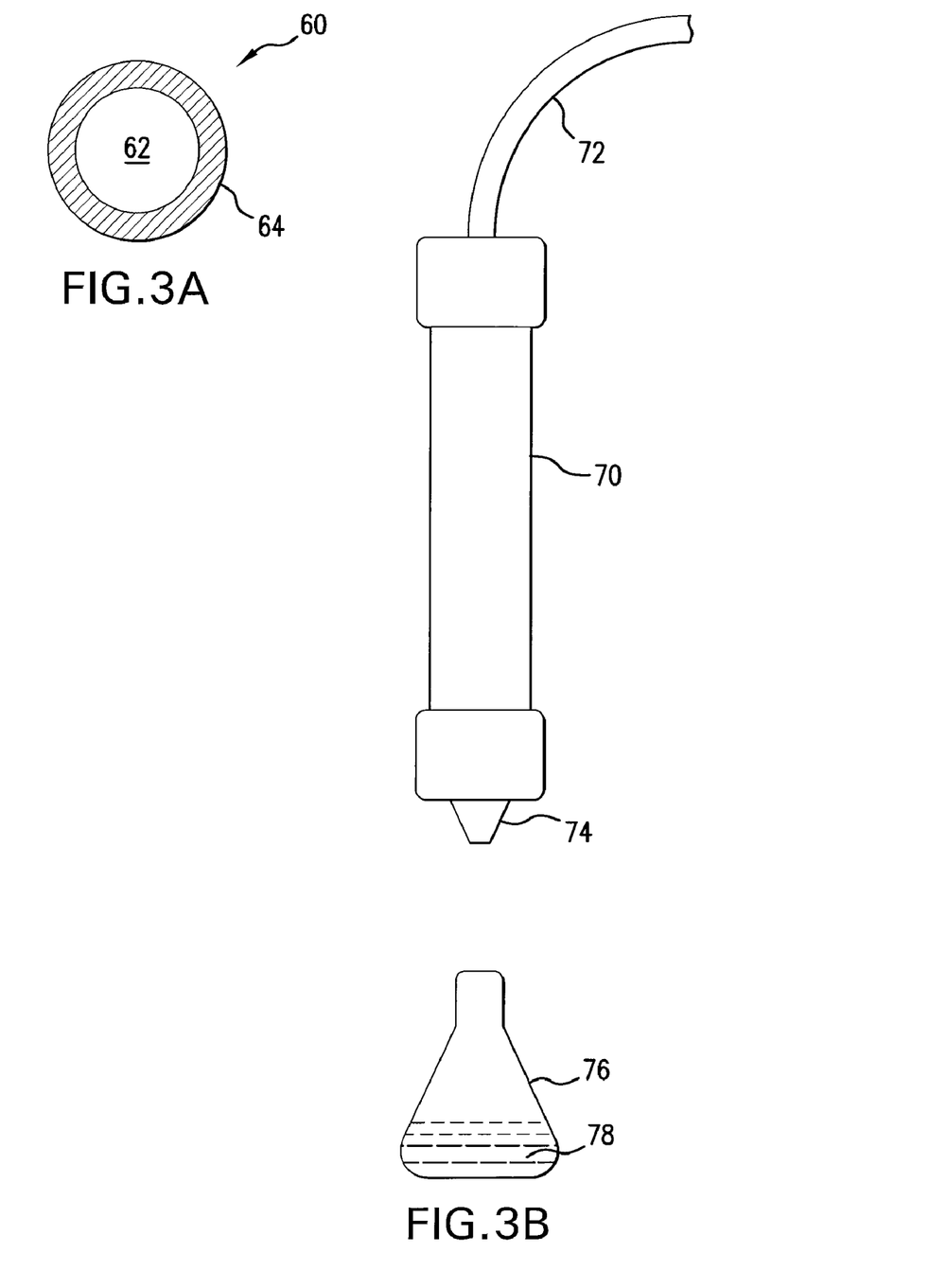
FIGS. 3A and 3B show a chromatography column according to yet another embodiment.

In certain embodiments, the imprinted polymeric material may be used in the separation and/or purification of biologic materials, such as proteins or viruses. For example, referring to the embodiment shown in FIGS. 3A and 3B, an imprinted polymeric material is packaged into a chromatography column for use in the purification of viruses. Referring to FIG. 3A, an absorbent bead 60 has a polystyrene core 62 (or other substrate conventionally used in chromatography columns) and the imprinted polymeric material is applied as a resin layer 64 on the surface of polystyrene core 62. A plurality of beads 60 are packed into a chromatography column 70 having an inlet 72 and an outlet 74. A cellular or tissue extract containing the target virus is loaded onto chromatography column 70 via inlet 72. In this setting, the imprinted polymeric material on beads 60 serves as an absorbent for the target virus in the chromatography column. As such, the imprinted polymeric material will preferentially bind the target viruses to the exclusion of other cellular or tissue components in the extract. By washing with an appropriate buffer solution, residual cellular or tissue components are washed away from chromatography column 70, leaving the desired target virus absorbed on the imprinted polymeric material covering beads 60. The target virus can then be eluted by washing chromatography column 70 with a second buffer having a different pH or ionic strength than the wash buffer. The eluted solution 78 containing the purified virus can be collected into a flask 76.

Notably, the purification of viruses using this method can eliminate many of the steps that are required in other conventional virus purification techniques. In fact, in some case, virus purification using the methods of the present invention may be performed in a matter of hours (compared to the several days that other virus purification techniques may require). Purified virus preparations have many possible uses. For example, certain applications, such as gene therapy or vaccine manufacture, often require large-scale quantities of purified virus. As such, this method of virus purification may be advantageous in reducing the time and expense needed for vaccine manufacture.

In certain embodiments, the imprinted polymeric material can be used in various blood processing treatments, such as hemofiltration, hemodialysis, dialysis, hemodiafiltration, plasmapheresis, or apheresis. In some cases, the imprinted polymeric material may be packaged into cartridges (e.g., as a filter or dialysis membrane) that are used in various conventional therapeutic blood processing systems. For example, the imprinted polymeric material may be packaged in a blood/plasma filter cartridge for use in a hemofiltration apparatus to absorb and eliminate viruses in a patient's blood/plasma. Such a treatment can be used to reduce viral loads in patients infected with a virus, such as HIV As mentioned above, various types of template articles may be used with the present invention. Further examples of template articles include biologic materials such as proteins, glycoproteins, lipoproteins, enzymes, antibodies, saccharides, peptides, polynucleotides, polypeptides, whole cells, and viruses. Examples of viruses include hepatitis A, hepatitis B, hepatitis C, HIV, influenza, parvovirus B19, foot and mouth disease virus, baculovirus, human papilloma virus, and varicella-zoster virus.

A reference to an element by the indefinite article "a" or "an" does not exclude the possibility that more than one of the element is present. Rather, the article "a" or "an" is intended to mean one or more (or at least one) unless the text expressly indicates otherwise. The terms "first," "second," and so on, when referring to an element, are not intended to suggest a location or ordering of the elements. Rather, the terms are used as labels to facilitate discussion and distinguish elements from one another.

The foregoing description and examples have been set forth merely to illustrate the invention and are not intended to be limiting. Each of the disclosed aspects and embodiments of the present invention may be considered individually or in combination with other aspects, embodiments, and variations of the invention. Modifications of the disclosed embodiments incorporating the spirit and substance of the invention may occur to persons skilled in the art and such modifications are within the scope of the present invention.

We claim:

1. An imprinted polymeric material comprising a cross-linked polymer matrix having a binding cavity capable of selectively binding a template article, wherein the polymer matrix comprises a polyampholyte polymer having monomer units at molar ratios that substantially complement the charge ratio of the template article.

2. The imprinted polymeric material of claim 1, wherein the geometry of the binding cavity is complementary to the geometry of the template article.

3. The imprinted polymeric material of claim 1, wherein the polymer matrix comprises functional groups that are spatially arranged around the binding cavity at locations that are complementary to functional groups on the template article.

4. The imprinted polymeric material of claim 3, wherein the functional groups on the polymer matrix are capable of interacting with the complementary functional groups on the template article.

5. The imprinted polymeric material of claim 1, wherein the size of the binding cavity is between 1 nm to 1 μm as measured along the longest axis of the binding cavity.

6. The imprinted polymeric material of claim 1, wherein the size of the binding cavity is between 10 nm to 500 nm as measured along the longest axis of the binding cavity.

7. The imprinted polymeric material of claim 1, wherein the polyampholyte polymer comprises a monomer unit that is a strong acid.

8. The imprinted polymeric material of claim 7, wherein the monomer unit is 2-acrylamidopropyl-2-methylpropane sulfonic acid (AMPSA).

9. The imprinted polymeric material of claim 1, wherein the polyampholyte polymer comprises a monomer unit that is a weak acid.

10. The imprinted polymeric material of claim 9, wherein the monomer unit is acrylic acid, maleic acid, 2-aminomethacrylate hydrochloride (AMA), or 2-dimethylaminoethyl methacrylate (DMAEMA).

11. The imprinted polymeric material of claim 1, wherein the polyampholyte polymer comprises a monomer unit that is a strong base.

12. The imprinted polymeric material of claim 11, wherein the monomer unit is 3-acrylamidopropyl trimethylammonium chloride (AMPTAC).

13. The imprinted polymeric material of claim 1, wherein the polyampholyte polymer comprises a monomer unit that is a weak base.

14. The imprinted polymeric material of claim 13, wherein the monomer unit is 3-N-aminopropylmethacrylamide or dimethyl aminoethylmethacrylate.

15. The imprinted polymeric material of claim 1, wherein the polyampholyte polymer comprises a monomer unit that is neutral.

16. The imprinted polymeric material of claim 15, wherein the monomer unit is acrylamide (Am), N-tertbutylacrylamide (NTBAAm), N-isopropylacrylamide (NIPAAm), or N,N'-dimethylacrylamide (DMAAm).

17. The imprinted polymeric material of claim 1, wherein the binding capacity of the imprinted polymeric material for the template article is at least 2-fold greater than the binding capacity of a control imprinted polymeric material having a cross-linked polyampholyte polymer matrix which lacks a binding cavity capable of selectively binding to the template article.

18. The imprinted polymeric material of claim 1, wherein the template article is a virus.

19. The imprinted polymeric material of claim 18, wherein the binding capacity of the imprinted polymeric material for the virus is at least 4-fold greater than the binding capacity of the imprinted polymeric material for another virus having a different geometric structure.

20. The imprinted polymeric material of claim 1, wherein the template article is a microorganism.

21. The imprinted polymeric material of claim 1, wherein the template article is a biologic macromolecule.

22. A method of forming an imprinted polymeric material, comprising:
providing a template article in an aqueous solution;
adding a first monomer unit to the aqueous solution, wherein the first monomer unit exhibits an electrostatic charge in the aqueous solution;
adding a second monomer unit to the aqueous solution, wherein the second monomer unit is different from the first monomer unit and the monomer units are at molar ratios that substantially complement the charge ratio of the template article;
forming a polymer matrix containing the template article, wherein the step of forming the polymer matrix comprises polymerizing the monomer units; and
removing the template article from the polymer matrix.

23. The method of claim 22, wherein the second monomer unit is neutral or exhibits an electrostatic charge opposite to that of the first monomer unit.

24. The method of claim 22, wherein the first and second monomer units are added sequentially to the aqueous solution.

25. The method of claim 24, wherein the first monomer unit is added before the second monomer unit.

26. The method of claim 24, wherein the second monomer unit is added before the first monomer unit.

27. The method of claim 22, wherein the first and second monomer units are added simultaneously to the aqueous solution.

28. The method of claim 22, further comprising adding a third monomer unit to the aqueous solution, wherein the third monomer unit is different from both the first monomer unit and the second monomer unit.

29. The method of claim 28, wherein one of the three monomer units exhibits a positive charge in the aqueous solution, another of the three monomer units exhibits a negative charge in the aqueous solution, and yet another of the three monomer units is neutral in the aqueous solution.

30. The method of claim 29, wherein the molar ratio of positively-charged:negatively-charged:neutral monomer units is substantially the same as the ratio of negatively-charged:positively-charged:neutral functional groups on the exposed surface of the template article.

31. The method of claim 22, wherein the aqueous solution is at a pH level that allows the first monomer unit to exhibit the electrostatic charge and allows the template article to exhibit at least one electrostatic charge that is opposite to the electrostatic charge on the first monomer unit.

32. The method of claim 22, wherein forming the polymer matrix further comprises cross-linking the polymers that result from the polymerization of the monomer units.

33. The method of claim 22, wherein removing the template article forms a binding cavity in the polymer matrix, wherein the binding cavity is capable of selectively binding to the template article.

34. The method of claim 22, wherein removing the template article is performed by solvent extraction.

35. An article of manufacture comprising the imprinted polymeric material of claim 1.

36. The article of manufacture of claim 35, further comprising a cartridge for use in blood or plasma processing, and wherein the cartridge contains the imprinted polymeric material.

37. The article of manufacture of claim 36, wherein the cartridge is a dialysis cartridge.

38. The article of manufacture of claim 36, wherein the cartridge is a blood or plasma filter cartridge.

39. The article of manufacture of claim 35, further comprising a chromatography column, wherein the chromatography column contains the imprinted polymeric material.

40. The article of manufacture of claim 35, further comprising a sensor for sensing the presence of the template article bound to the imprinted polymeric material.

41. The article of manufacture of claim 40, further comprising a medical diagnostic apparatus comprising the sensor.

42. A method of purifying a virus extract, comprising:
providing a virus extracted from a cellular or tissue source;
providing a chromatography column containing the imprinted polymeric material of claim 1;
loading the virus extract onto the chromatography column;
washing the chromatography column; and
eluting the virus from the chromatography column.

43. A method of producing a vaccine, comprising:
purifying a virus according to the method of claim 42; and
using the purified virus to produce a vaccine against the virus.

44. An imprinted polymeric material comprising a cross-linked polymer matrix having a binding cavity capable of selectively binding a template article, wherein the polymer matrix comprises a polyampholyte polymer having monomer units at molar ratios that substantially complement the charge ratio of the template article and wherein the polyampholyte polymer includes a monomer unit that is a weak acid.

45. An imprinted polymeric material obtained by the method of claim 22.

* * * * *